United States Patent [19]

Drake et al.

[11] 4,001,294
[45] Jan. 4, 1977

[54] METHOD OF PREPARING UNSATURATED DINITRILES

[75] Inventors: Charles A. Drake; Stanley J. Marwil, both of Bartlesville, Okla.

[73] Assignee: Phillips Petroleum Company, Bartlesville, Okla.

[22] Filed: Oct. 20, 1975

[21] Appl. No.: 624,023

[52] U.S. Cl. .................. 260/465.8 R; 260/465.9
[51] Int. Cl.² .............. C07C 120/00; C07C 121/20
[58] Field of Search ............ 260/465.8 R, 465.8 D, 260/465.9

[56] References Cited

UNITED STATES PATENTS

| | | | |
|---|---|---|---|
| 2,641,607 | 6/1953 | Albisetti et al. | 260/465.3 |
| 3,393,165 | 7/1968 | Evans et al. | 260/22 |
| 3,840,583 | 10/1974 | Turk et al. | 260/465.8 R |
| 3,898,268 | 8/1975 | Drake | 260/465.9 |
| 3,929,860 | 12/1975 | Drake | 260/465.9 |

OTHER PUBLICATIONS

Rebenfeld; Ency. of Polymer Science and Tech., vol. 6, (1967), pp. 520–522.

Sweeny, et al; Ency. of Polymer Science and Tech., vol. 10, (1969), pp. 524–526.

Bannerman, et al; Polymer Processes, (1956), pp. 276–278.

Deanin, Polymer Structure–Properties and Application, (1972), pp. 455–456.

Fuson; Reactions of Organic Compounds, (1962), p. 275.

Fieser, et al; Advanced Organic Chemistry, (1961), p. 542.

Albisetti, et al; J.A.C.S., 78(1956), pp. 2637–2641.

Billmeyer, Jr.; Textbook of Polymer Science, 2nd ed., (1971), p. 243.

Primary Examiner—Joseph Paul Brust

[57] ABSTRACT

In processes of preparing mixed, isomeric $C_{10}$ unsaturated dinitriles from acrylonitrile and isobutylene in which 5-methyl-4-hexenenitrile is formed, the method of inhibiting the formation of that compound comprising conducting the preparation of the $C_{10}$ unsaturated dinitriles in the presence of a sufficient amount of an alkali metal salt of an (alkylenedinitrilo)tetracarboxylic acid, such as (ethylenedinitrilo)tetraacetic acid.

17 Claims, No Drawings

METHOD OF PREPARING UNSATURATED DINITRILES

This invention relates to an improved process for the preparation of unsaturated dinitriles. In another aspect, it relates to processes for producing $C_{10}$ dinitriles from acrylonitrile and isobutylene. In still another aspect it relates to a method of producing mixed isomeric $C_{10}$ dinitriles useful for producing fiber grade polyamides.

Fundamentally, dinitriles in general have been of interest for many years as precursors to the corresponding dicarboxylic acids and diamines which, in turn, are important reactants for preparing condensation polymers. An example is the well-known condensation between diacids and diamines to produce polyamides.

Certain mixed isomeric $C_{10}$ unsaturated dinitriles that can be synthesized by the twofold addition of acrylonitrile to isobutylene are of particular interest in reference to the production of fiber grade polyamides. Various methods of carrying out such a twofold addition are known in the art including the methods described in S. D. Turk et al in U.S. Pat. 3,840,583 (1974), C. J. Albisetti et al in U.S. Pat. No. 2,641,607 (1953) and in *J. Am. Chem. Soc.* 78, pp. 2637–2641 (1956).

U.S. Pat. No. 2,641,607 (1953) and *J. Am. Chem. Soc.* 78, pp. 2637–2641 (1956), the disclosures of which are incorporated herein by reference, describe the preparation of $C_{10}$ unsaturated dinitriles by reacting acrylonitrile with isobutylene to produce unsaturated mononitriles which are recovered and reacted with additional acrylonitrile to yield the $C_{10}$ unsaturated dinitriles.

S. D. Turk et al in U.S. Pat. No. 3,840,583 (1974), the disclosure of which is incorporated herein by reference, also disclose two other methods by which $C_{10}$ unsaturated dinitriles can be prepared from isobutylene and acrylonitrile. One method involves reacting isobutylene with enough acrylonitrile to insure that there is acrylonitrile present which can react with the unsaturated mononitrile that is formed. Another method disclosed in the above-mentioned Turk et al patent is a single stage reaction involving the concurrent contacting of acrylonitrile, isobutylene and a monoadduct reaction product of isobutylene and acrylonitrile, wherein there is a significant amount of monoadduct present during substantially the entire reaction period.

Each of the above-discussed methods of synthesizing mixed, isomeric $C_{10}$ unsaturated dinitriles can be viewed as involving the twofold addition of acrylonitrile to isobutylene, that is, acrylonitrile and isobutylene react to produce mixed, isomeric unsaturated $C_7$ mononitriles which react with an additional equivalent of acrylonitrile to yield the $C_{10}$ unsaturated dinitriles. As a matter of convenience in this disclosure mononitriles produced from the reaction of acrylonitrile and isobutylene will be referred to as "monoadduct" and the term "diadduct" will be used to denote dinitrile products.

In the synthesis of the $C_{10}$ unsaturated dinitriles the monoadduct generally comprises 5-methyl-5-hexenenitrile as the principal product along with a small amount of 2,4-dimethyl-4-pentenenitrile. The resulting diadduct generally comprises 5-methylene-1,9-nonanedinitrile, 5-methyl-4-nonenedinitrile, 2-methyl-4-methyleneoctanedinitrile, 2,6-dimethyl-4-heptanedinitrile, and 2,4,6-trimethyl-3-heptenedinitrile.

In the preparation of $C_{10}$ diadduct from acrylonitrile and isobutylene it has been observed that the isomer 5-methyl-4-hexenenitrile may also be an intermediate product. For example, in preparing diadduct via a single stage reaction which involves contacting isobutylene, acrylonitrile, and a monoadduct reaction product of isobutylene and acrylonitrile, wherein there is monoadduct reaction product present in significant amounts during substantially the entire reaction period, it has been discovered that there is a buildup of 5-methyl-4-hexenenitrile when the monoadduct that is produced is repeatedly recycled. Also when recovered acrylonitrile is recycled along with recovered monoadduct, the increase in 5-methyl-4-hexenenitrile has been observed to be even greater.

One skilled in chemistry will recognize that in the reaction of 5-methyl-4-hexenenitrile with acrylonitrile the major expected product is 4-isopropenyl-1,7-heptanedinitrile, which has a bulky three-carbon atom branch in its chain. In contrast, when 5-methyl-5-hexenenitrile is reacted with acrylonitrile the major product is 5-methylene-1,9-nonanedinitrile, which contains only a single carbon atom side branch.

It is also well recognized that in order to prepare good fiber grade polyamides it is desirable that the monomers be linear and without bulky side groups. This is taught, for example, by Fred W. Billmeyer, Jr., *Textbook of Polymer Science*, Second Edition, Wiley-Interscience, New York (1971), p. 243; Ludwig Rebenfeld, *Ency. of Polymer Sci. and Tech.*, Vol. 6, Interscience Publishers, New York (1967), pp. 520–522; W. Sweeny and J. Zimmerman, *Ency. of Polymer Sci. and Tech.*, Vol. 10, Interscience Publishers, New York (1969), pp. 524–526; B. G. Bannerman and E. E. Magat, *Polymer Processes*, Calvin E. Schildknecht, Ed., Interscience Publishers, New York (1956), pp. 276–278; and Rudolph D. Deanin, *Polymer Structure, Properties and Application*, Cahner Books, Boston (1972), pp. 455–456. In view of the teachings of those publications it should be clear that in producing $C_{10}$ dinitriles which are to be employed in producing fiber grade polyamides it is preferable to minimize the formation of 4-isopropenyl-1,7-heptanedinitrile. Thus it follows that in the preparation of $C_{10}$ dinitriles from acrylonitrile and isobutylene, one method of minimizing the formation of the undesired dinitrile is to minimize the formation of 5-methyl-4-hexenenitrile. As little as 0.5 weight percent of the monoadduct being 5-methyl-4-hexenenitrile will adversely affect the fiber-forming properties of polymers derived from the diadduct. Therefore an object of this invention is to minimize the formation of 5-methyl-4-hexenenitrile in processes of preparing mixed, isomeric $C_{10}$ dinitriles by the twofold addition of acrylonitrile to isobutylene.

A further object is to provide a process for preparing mixed, isomeric $C_{10}$ unsaturated dinitriles in which the formation of $C_{10}$ unsaturated dinitriles unsuitable for the production of fiber grade polyamides is minimized.

It has been surprisingly discovered that in the preparation of mixed, isomeric $C_{10}$ unsaturated dinitriles by the twofold addition of acrylonitrile to isobutylene the formation of 5-methyl-4-hexenenitrile can be inhibited by the presence of a small but sufficient amount of at least one alkali metal salt represented by the general formula:

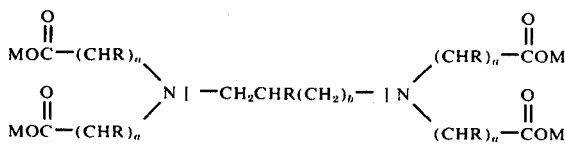

wherein
each M is individually selected from the group consisting of hydrogen and an alkali metal such that at least one M is an alkali metal atom, e.g. lithium, sodium, potassium, rubidium or cesium,
each R is individually selected from the group consisting of hydrogen, methyl, and ethyl such that the total number of carbon atoms per molecule is in the range of 10 to 21,
$a$ is an integer of value 1 or 2, and
$b$ is an integer of value 0 or 1.

Examples include (ethylenedinitrilo)tetraacetic acid trisodium salt, (1,2-butylenedinitrilo)tetraacetic acid tetrapotassium salt, (1,2-propylenedinitrilo)tetrapropionic acid monocesium salt, (ethylenedinitrilo)triacetic acid propionic acid tetralithium salt, (2-ethyl-1,3-propylenedinitrilo)tetra(ethylacetic) acid tetrasodium salt, (ethylenedinitrilo)tetraacetic acid dirubidium salt, and mixtures thereof.

The formation of 5-methyl-4-hexenenitrile during the preparation of mixed, isomeric $C_{10}$ unsaturated dinitriles is inhibited by providing that the reaction mixture contain a sufficient amount of the above-identified alkali metal salt at a point in the reaction where 5-methyl-4-hexene is observed to form. Any suitable inhibiting amount of the above-described alkali metal salt can be employed in this invention. Of course, upper desirable limits on the amount of salt employed may be determined by practical considerations, such as cost, recovery of products, undesired effects on the reaction, etc. Optimum amounts of the chosen alkali metal salt for a particular process can be determined by those skilled in the art by routine experimentation. Generally the amount of alkali metal salt inhibitor employed is in the range of about 0.005 to about 1.25 percent of all the materials present in the reaction zone excluding said alkali metal salt. Preferably the amount of alkali metal salt inhibitor employed is in the range of about 0.01 to about .25 percent of the weight of all the materials present in the reaction zone excluding said alkali metal salt.

In a preferred embodiment of this invention an (alkylenedinitrilo)tetracarboxylic acid salt as described above is employed to inhibit the formation of 5-methyl-4-hexenenitrile in a process of producing $C_{10}$ unsaturated dinitriles which involves using recycled monoadduct or recycled monoadduct and recycled acrylonitrile in the concurrent reaction of isobutylene, acrylonitrile, and monoadduct of isobutylene and acrylonitrile, wherein there is a significant amount of monoadduct present during substantially all of the reaction period.

As pointed out in U.S. Pat. No. 3,840,583 any suitable amount of isobutylene, acrylonitrile, and monoadduct reaction product can be employed in the concurrent method of preparing $C_{10}$ unsaturated dinitriles. In general the mole ratio of acrylonitrile to isobutylene will be in the range of about 10:1 to about 0.1:1, preferably in the range of about 5:1 to about 0.2:1, and more preferably in the range of about 2:1 to about 0.3:1. In general the monoadduct reaction product will be employed in an amount such that during substantially the entire reaction period the net monoadduct reaction product present in the reaction mixture will constitute from about 10 to about 90, preferably from about 20 to about 80, and more preferably from about 30 to about 70 weight percent of the total reaction mixture. The net amount of monoadduct reaction product present in the reaction zone is the sum of the amount of monoadduct reaction product charged to the reaction zone plus the amount of monoadduct reaction product produced by the reaction of isobutylene and acrylonitrile in the reaction zone less the monoadduct reaction product consumed in the reaction zone as by being converted to diadduct by reaction with the acrylonitrile present in the reaction zone. As used herein the total reaction mixture includes all materials present in the reaction zone, i.e., reactants, diluents, products, by-products, etc., less the inhibiting alkali metal salt contained in the reaction mixtures.

As pointed out in U.S. Pat. No. 3,840,583 the reaction time, temperature, and pressures employed in such a process can vary widely. Any suitable reaction conditions for either a batch process or a continuous process can be employed.

Generally a time period of from about 2 minutes to about 48 hours, preferably from about 30 minutes to about 10 hours, and more preferably from about 1 hour to about 5 hours is an adequate period of time for the reactants to be suitably admixed in the preparation of reaction products in high yields in a batch process. In a continuous process the liquid hourly space velocity (volume of reactants/volume of reactor/hour) will generally be in the range of about 0.05 to about 20, preferably in the range of about 0.1 to about 10, more preferably in the range of about 0.5 to about 2.

Generally suitable reaction temperatures are within the range of from about 100° to about 500° C., and preferred reaction temperatures are within the range of from about 200° to about 350° C.

Reaction pressures within a range of from about 0 psig (atmospheric pressure) to about 100,000 psig can be employed; however, reaction pressures within the range of from about 500 psig to about 4000 psig are preferably employed.

This concurrent reaction method of producing $C_{10}$ unsaturated dinitriles can be carried out in the presence of or the absence of a polymerization inhibitor. The presence of a polymerization inhibitor often advantageously limits or restricts side reactions within the reaction media such as the dimerization or polymerization of the olefinically unsaturated mononitrile present in the reaction zone.

Generally, the inhibitor, when used, can be employed in amounts of from about 0.001 to about 5, preferably from about 0.1 to about 1 percent by weight, based on the olefinically unsaturated mononitrile reactant. Suitable inhibitors include hydroquinone, 2,6-di-tert-butyl-4-methylphenol, 2,6-di-tert-butylhydroquinone, 4-tert-butylcatechol, para-hydroxydiphenylamine, and the like, and combinations thereof.

The reaction of the three reactants can be carried out in the presence of a solvent or a diluent which is nonreactive with either the reactants or the reaction products. Representative of the commercially available nonreactive solvents that can be employed are the following: benzene, toluene, p-xylene, o-xylene, m-xylene, ethylbenzene, diethyl ether, ethyl propyl ether, dibutyl ether, tetrahydrofuran, dioxane, cyclohexane, carbon tetrachloride, methylene chloride, and the like, and mixtures thereof. Although a nonreactive solvent or diluent can be employed in the reaction it is not necessary that such be employed.

Any suitable amount of (alkylenedinitrilo)tetracarboxylic acid alkali metal salt can be employed to inhibit the formation of 5-methyl-4-hexenenitrile in such a concurrent reaction process. Generally in such a concurrent reaction the alkali metal salt is employed in such an amount that the mole ratio of monoadduct reactant to salt is in the range of from about 6000:1 to about 200:1. More preferably the salt is employed in such an amount that the mole ratios are in the range of about 4000:1 to about 1000:1.

The advantage of using agents such as the described (alkylenedinitrilo)tetracarboxylic acid salts during the preparation of unsaturated dinitriles is demonstrated by the following examples.

EXAMPLE I

Several runs were made producing mixed, isomeric $C_{10}$ unsaturated dinitriles. The runs were conducted using a system in which all the metal surfaces were 316 stainless steel. The procedure employed, involving the specifics shown in Table I, required charging acrylonitrile and monoadducts to a 1-liter stainless steel autoclave, flushing the system with prepurified nitrogen to exclude atmospheric oxygen, charging with isobutylene and heating under autogeneous pressure at the times and temperatures shown in the table. The product mixture was cooled and vented to remove unreacted isobutylene. The resulting product was distilled through a packed column to isolate the monoadduct (120°–130° C at 120 mm). The monoadduct was then analyzed by gas-liquid chromatography. In these runs at least part of the monoadduct employed was that recovered from similar previous addition reactions. Also in some of the runs at least part of the acrylonitrile employed was that recovered from similar previous addition reactions. In Runs 1–6 no recycle acrylonitrile was employed. In Runs 7–9, recycled acrylonitrile was employed as at least part of the acrylonitrile used. In Runs 6 and 9, the (ethylenedinitrilo)tetraacetic acid trisodium salt was charged to the reactor after the monoadduct had been added and prior to flushing the system with prepurified nitrogen.

TABLE I

| Run No. | Acrylo-nitrile | Mono-adduct | Iso-butylene | Na₃ EDTA[1] | Recycle Acrylo-nitrile | Reaction Conditions °C/hrs. | Degree of Isomerization of Monoadduct As Charged, Wt. % | Degree of Isomerization Monoadduct at the End of the Reaction, wt. % |
|---|---|---|---|---|---|---|---|---|
| 1 | 64 | 131 | 200 | 0 | No | 270/3 | 0.8 | 1.04 |
| 2 | 85 | 471 | 80 | 0 | No | 270/3 | 0.51 | 0.64 |
| 3 | 85 | 365 | 190 | 0 | No | 270/2 | 0.65 | 0.81 |
| 4 | 85 | 365 | 190 | 0 | No | 270/2 | 0.79 | 0.88 |
| 5 | 85 | 365 | 190 | 0 | No | 270/2 | 0.90 | 1.09 |
| 6 | 85 | 365 | 190 | 0.5 | No | 270/2 | 0.81 | 0.79 |
| 7 | 85 | 365 | 190 | 0 | Yes | 270/2 | 1.086 | 1.57 |
| 8 | 85 | 365 | 190 | 0 | Yes | 270/2 | 1.142 | 1.65 |
| 9 | 85 | 365 | 190 | 0.5 | Yes | 270/2 | 1.14 | 1.16 |

[1](ethylenedinitrilo)tetraacetic acid trisodium salt.

In Table I the degree of isomerization in the monoadduct as charged can be compared to the degree of isomerization in the monoadduct present in the product mixture. The degree of isomerization was determined by gas-liquid chromatography. The degree of isomerization is indicated as the weight percent of monoadduct that is 5-methyl-4-hexenenitrile. Runs 1–5 employing recycled monoadduct each showed a definite increase in isomerization of the monoadduct during the reaction. In Runs 7 and 8 in which both monoadduct and acrylonitrile were recycled, the increase in percent of isomerization of monoadduct was even greater than it was in Runs 1–5. Run 6 shows that when recycled monoadduct is employed and recycled acrylonitrile is not employed the presence of (ethylenedinitrilo)tetraacetic acid trisodium salt inhibits isomerization of the monoadduct. Run 9 shows that when both monoadduct and acrylonitrile are recycled the presence of the tetraacetic acid trisodium salt substantially inhibits an increase in isomerization of the monoadduct.

EXAMPLE II

Using the system used in Example I, runs were made in which acrylonitrile and (ethylenedinitrilo)tetraacetic acid trisodium salt were charged to the 1-liter stainless steel autoclave which was then flushed with prepurified nitrogen to exclude atmospheric oxygen, followed by the addition of isobutylene and heating under autogeneous pressure at the time and temperatures shown in Table II.

TABLE II

| Run No. | Acrylo-nitrile | Iso-butylene | Na₃ EDTA[1] | Solvent Benzene ml. | Recycle Acrylo-nitrile | Reaction Conditions °C/hrs | Degree of Isomerization of Monoadduct at the End of Reaction, wt. % |
|---|---|---|---|---|---|---|---|
| 10 | 50 | 280 | 0.5 | 100 | No | 260/2.5 | 0.2 |
| 11 | 53 | 220 | 0.5 | None | No | 270/2 | 0 |
| 12 | 50 | 280 | 0.5 | 100 | Yes | 260/2.5 | 0.2 |

[1](Ethylenedinitrilo)tetraacetic acid trisodium salt.

Table II shows that only a negligible degree of isomerization of monoadduct occurred when the (ethylenedinitrilo)tetraacetic acid trisodium salt was employed. The effect was obtained when recycled acrylonitrile was employed as well as when nonrecycled acrylonitrile was employed.

The foregoing examples have been provided merely to enable one skilled in the art to understand the invention and to demonstrate to those skilled in the art the effectiveness of compounds such as (ethylenedinitrilo)-tetraacetic acid trisodium salt in inhibiting the formation of 5-methyl-4-hexenenitrile during the preparation of mixed, isomeric $C_{10}$ unsaturated dinitriles by the twofold addition of acrylonitrile to isobutylene. Reasonable variation and modifications of the process of this invention are considered to be within the scope of the invention.

What is claimed is:

1. A method for inhibiting the formation of 5-methyl-4-hexenenitrile during the preparation of mixed, isomeric $C_{10}$ unsaturated dinitriles by the twofold addition of acrylonitrile to isobutylene under reaction conditions suitable for producing said isomeric $C_{10}$ unsaturated dinitriles comprising providing that the reaction mixture contain, at a point in the reaction where 5-methyl-4-hexenenitrile is found to form, in an amount sufficient to inhibit the formation of 5-methyl-4-hexenenitrile, an alkali metal salt of the formula

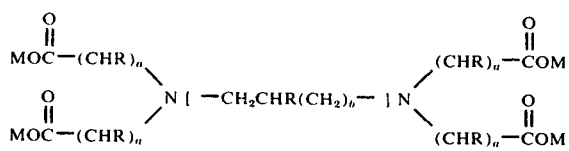

wherein
each M is individually selected from the group consisting of hydrogen and an alkali metal such that at least one M is an alkali metal atom,
each R is individually selected from the group consisting of hydrogen, methyl, and ethyl such that the total number of carbon atoms per molecule is in the range of 10 to 21,
$a$ is an integer of value 1 or 2, and
$b$ is an integer of value 0 or 1.

2. A method according to claim 1 wherein the $C_{10}$ unsaturated dinitriles are produced by reacting acrylonitrile and isobutylene to form monoadduct, separating the monoadduct, and then reacting the monoadduct with additional acrylonitrile.

3. A method according to claim 1 wherein said alkali metal salt is employed in the reaction mixture in an amount within the range of about 0.005 to about 1.25 percent of the weight of all the materials in the reaction mixture excluding said alkali metal salt.

4. A method according to claim 1 wherein the $C_{10}$ unsaturated dinitriles are produced by reacting isobutylene with enough acrylonitrile to insure that some of the monoadduct mixture formed will be converted to unsaturated dinitrile.

5. A method according to claim 1 wherein the unsaturated dinitriles are prepared by concurrently contacting acrylonitrile, isobutylene, and monoadduct.

6. A method according to claim 5 wherein the mole ratio of acrylonitrile to isobutylene is within the range of about 10 to 1 to about 0.1 to 1 and the concentration of the monoadduct in the reaction mixture is within the range of from about 10 to about 90 weight percent, based on the total weight of the reaction mixture less the weight of said inhibiting alkali metal salt in said reaction mixture.

7. A method according to claim 6 wherein the mole ratio of the monoadduct to the alkali metal salt is in the range of about 6000 to 1 to about 200 to 1.

8. A method according to claim 7 wherein at least a part of the monoadduct employed is the monoadduct recovered from the product mixture of a concurrent reaction of acrylonitrile, isobutylene, and monoadduct.

9. A method according to claim 7 wherein the mole ratio of the monoadduct to the alkali metal salt is in the range of about 4000 to 1 to about 1000 to 1.

10. A method according to claim 5 wherein the alkali metal salt is (ethylenedinitrilo)tetraacetic acid trisodium salt.

11. A method according to claim 5 wherein at least part of the monoadduct employed is the monoadduct recovered from the product mixture of a concurrent reaction of acrylonitrile, isobutylene, and monoadduct.

12. A method according to claim 11 wherein at least part of the acrylonitrile employed is the acrylonitrile recovered from the product mixture of a concurrent reaction of acrylonitrile, isobutylene, and monoadduct.

13. A method according to claim 7 wherein said acrylonitrile, isobutylene, and monoadduct are concurrently contacted for a time in the range of about 2 minutes to about 10 hours under pressure in the range of atmospheric pressure to about 100,000 psig and temperature in the range of about 100° to about 500° C.

14. A method according to claim 13 wherein the alkali metal salt is (ethylenedinitrilo)tetraacetic acid trisodium salt.

15. A method according to claim 1 wherein the alkali metal salt is (ethylenedinitrilo)tetraacetic acid trisodium salt.

16. A method according to claim 15 wherein said alkali metal salt is employed in the reaction mixture in an amount within the range of about 0.005 to about 1.25 percent of the weight of all the materials in the reaction excluding said alkali metal salt.

17. A method according to claim 16 wherein said acrylonitrile, isobutylene, and monoadduct are concurrently contacted for a time in the range of about 2 minutes to about 10 hours under pressure in the range of atmospheric pressure to about 100,000 psig and temperature in the range of about 100° to about 500° C.

* * * * *